US006913205B2

(12) United States Patent
Cornet et al.

(10) Patent No.: US 6,913,205 B2
(45) Date of Patent: Jul. 5, 2005

(54) FLUID PRODUCT DISTRIBUTOR

(75) Inventors: Gérard Cornet, Blaru (FR); Firmin Garcia, Evreux (FR)

(73) Assignee: Valois S.A.S., Le Neubourg (FR)

( * ) Notice: Subject to any disclaimer, the term of this patent is extended or adjusted under 35 U.S.C. 154(b) by 279 days.

(21) Appl. No.: 10/283,181

(22) Filed: Oct. 30, 2002

(65) Prior Publication Data

US 2003/0094505 A1 May 22, 2003

Related U.S. Application Data

(60) Provisional application No. 60/342,408, filed on Dec. 27, 2001.

(30) Foreign Application Priority Data

Oct. 30, 2001 (FR) .......................................... 01.14067

(51) Int. Cl.[7] .......................... A24F 25/00; A61L 9/04

(52) U.S. Cl. ...................... 239/44; 239/102.1; 239/37; 239/338; 239/326; 128/200.16; 128/200.22; 128/200.23; 128/200.12

(58) Field of Search ........................ 239/44, 326, 338; 128/200.16, 200.22, 200.23, 200.12

(56) References Cited

U.S. PATENT DOCUMENTS

| | | | | |
|---|---|---|---|---|
| 4,479,609 A | * 10/1984 | Maeda et al. | ............ | 239/102.2 |
| 5,261,601 A | * 11/1993 | Ross et al. | ............... | 239/102.2 |
| 5,515,842 A | 5/1996 | Ramseyer et al. | | |
| 5,529,055 A | * 6/1996 | Gueret | .................. | 128/200.16 |
| 6,659,364 B1 | * 12/2003 | Humberstone et al. | ........ | 239/4 |

FOREIGN PATENT DOCUMENTS

EP 0 642 802 B1 3/1995

* cited by examiner

*Primary Examiner*—David A. Scherbel
*Assistant Examiner*—James S. Hogan
(74) *Attorney, Agent, or Firm*—Sughrue Mion, PLLC

(57) ABSTRACT

The present invention concerns a fluid product distributor comprising a reservoir of fluid product (1), a distribution outlet, a distribution system (2) for distributing fluid product through the distribution outlet, and an activating button (3) to activate the means of distribution. The distribution further comprises a visible reservoir the distribution outlet and the activating button (3) being located on either side of the reservoir (1), such that the reservoir visibly extends between the distribution outlet and the activating button.

22 Claims, 2 Drawing Sheets

FLUID PRODUCT DISTRIBUTOR

CROSS REFERENCE TO RELATED APPLICATION

This application claims the benefit under 35 U.S.C. §119 (e) of U.S. provisional patent application Ser. No. 60/342, 408, filed Dec. 27, 2001, and priority under 35 U.S.C. §119(a)–(d) of French patent application No. FR-01.14067, filed Oct. 30, 2001.

TECHNICAL FIELD

The present invention relates to a fluid product distributor comprising a reservoir of fluid product, a distribution outlet, distribution means for distributing the fluid product extracted from the reservoir through the distribution outlet and an activating button for activating the distribution means. It concerns a classic and general distributor configuration, as can be found in the domain of cosmetics, perfumeries or pharmacies.

BACKGROUND OF THE INVENTION

In general, the fluid product reservoir comprises a base which serves as a support surface allowing the distributor to stand up in a stable manner. At the extremity opposite to the base, the reservoir forms a neck which defines an opening towards the interior of the reservoir. The distribution means, for example a pump or a valve, are mounted in the neck. In order to activate the distribution means, there is generally a push-button to be acted on for example by a finger in order to activate the distribution means so as to extract some of the fluid product in the reservoir. The fluid product thus taken is distributed through a distribution outlet which can, for example, be in the form of a spray. The general configuration of such a distributor according to prior art is therefore relatively simple, that is to say a reservoir constituting the lower part of the distributor, distribution means mounted on this reservoir and a push button located at the upper extremity of the distribution means. Evidently other forms of distributors exist in which the reservoir is located in the upper part of the distributor and the pump is located beneath the reservoir. This is the case, for example, in document U.S. Pat. No. 4,882,096. In all cases, the activating button is located close to the distribution means and the distribution outlet.

SUMMARY OF THE INVENTION

The aim of the present invention is to define another form or concept of fluid product distributor in which the activating button and the distribution outlet are totally dissociated such that the user does not notice any direct technical relation between the activating button and the distribution outlet.

In order to achieve this aim, the invention proposes that the reservoir is visible and the distribution outlet and the activating button are located on either side of the reservoir, such that the reservoir visibly extends between the distribution outlet and the activating button. Thus, the reservoir constitutes a distinct and apparently impassable separation between the activating button and the distribution outlet. This is even more marked when the reservoir is relatively elongated such that it forms a real elongated barrier separating the activating button and the distribution outlet.

According to an embodiment, the distributor comprises two lateral uprights on either side of the reservoir, one upright receiving the distribution outlet and the other upright receiving the activating button. Advantageously, the reservoir is made out of a transparent or translucent material. In fact, the user can then literally see through the reservoir and can immediately see that there is no connection between the activating button and the distribution outlet. This, in fact, provides the distributor with a remarkable and even amazing aesthetic effect because the user does not understand immediately in which way the activating button can have an effect on the distribution outlet, which gives a little "magic" to the distributor.

According to one embodiment, the uprights are linked together at the level of a base. The uprights are, for example, very elongated and are linked to the base which only forms a small lower part of the distributor. Preferably, the uprights and the base are made in the form of a body. In other terms the uprights form between them a deep elongated channel limited laterally by the uprights and below by the base, the reservoir being housed in this channel. The height of the uprights determines the depth of the channel, and the longer the uprights the more surprising the effect.

Advantageously, the base forms a support surface on which the distributor stands up in a stable manner with the uprights oriented substantially vertical. The distributor can then be in the shape of a column with constant cross-section or otherwise. In other terms, one can say that the uprights each comprise an extremity linked to the base and a free extremity.

According to another characteristic of the invention, the reservoir comprises an opening set in the base and a bottom located substantially at the level of the free extremities of the uprights. When the distributor is set on its base, the reservoir is set upside-down with its opening located below.

According to another characteristic of the invention, the distribution outlet defines a distribution axis and the activating button defines a push axis, the distribution axis and the push axis being parallel and advantageously aligned. Preferably, the distribution outlet and the activating button are located at the free extremities of the uprights. In this case, the surprising effect is at a maximum given that the reservoir separates the two uprights at the level of their free extremities and one has to go down to their lower ends connected to the base to find the place where they join. Thus the user has literally the impression that activating the button generates a supply of fluid product directly through the reservoir up to the distribution outlet, whereas in reality it is evidently necessary to bypass the reservoir by going around the base. The alignment of the axes contributes further to this surprising effect, given that the user immediately sees the alignment of these axes.

According to another characteristic of the invention, the distribution outlet comprises a vibrator plate perforated with several exit holes. Advantageously, the distribution means comprise drive means to vibrate the perforated plate.

According to another interesting characteristic of the invention, the distributor comprises a fluid product capillary supply system to bring fluid product from the reservoir to the perforated plate. Advantageously, the upright receiving the distribution outlet contains a capillary wick linking the reservoir to the perforated plate. Utilisation of a capillary wick associated with a vibrating perforated plate makes it possible to obtain an adequate supply of fluid product from the reservoir by choosing precisely the pore size of the wick and the diameter of the outlet holes from the perforated vibrating plate.

BRIEF DESCRIPTION OF THE DRAWINGS

The invention will now be described in more detail with reference to the attached drawings given as non-limiting examples of embodiments of the invention.

In the figures.

DESCRIPTION OF THE PREFERRED EMBODIMENTS

The fluid product distributor used to illustrate the present invention seen from the outside is in the form of a column intended to stand itself in a substantially vertical stable manner. The cross-section of the column can be uniform, for example square as in the case of FIG. 3. The column cross-section can also be non-uniform as in the case of embodiments in FIGS. 2*a* and 2*b*.

Externally, two constituent elements can be seen outside the distributor, that is a body 4 and a fluid product reservoir 1. The body 4 can be made of a mono-block, as in FIGS. 2*a* and 2*b*, but it can also be constituted of several parts, as in FIGS. 1 and 3. However, in every figure, the body 4 has or forms an activating button 3 and a distribution outlet 2. The activating button 3 serves as command organ to activate the distribution means housed in the body 4 and whose function is to distribute the fluid product through the distribution outlet 2. More simply, by pressing on the activating button 3, the fluid product is distributed at the level of the distribution outlet 2.

According to the invention, the fluid product reservoir 1 visibly extends between the activating button 3 and the distribution outlet 2. This is clearly visible in FIGS. 1 and 2*b*. With such an arrangement of the reservoir between the activating button and the distribution outlet, there is complete visual dissociation between the activating button and the distribution outlet since they are clearly separated by the reservoir 1. This provides the distributor with a surprising visual or aesthetic effect giving the distributor a "mysterious" or "magic" side. This is even more perceptible when the fluid product reservoir is made out of a transparent or translucent material such as glass or plastic. In fact, the user immediately notices that the activating button and the distribution outlet are separated by a mass of liquid which can be seen through the transparent or translucent wall of the reservoir.

Figure 2C:
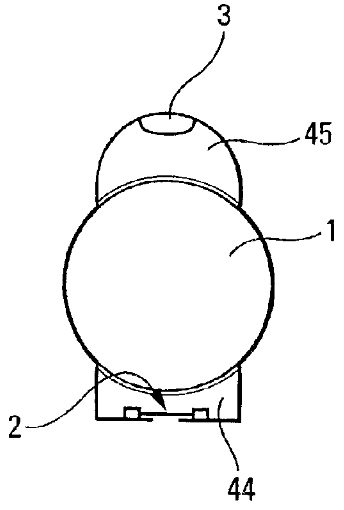
FIG. 2*c* is a cross-section along the line C—C of FIG. 2*b*.
Figure 3:
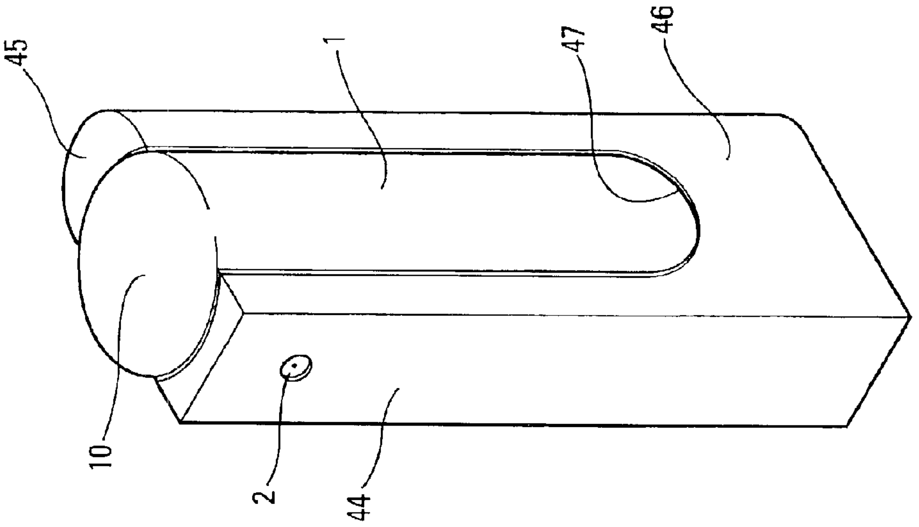
FIG. 3 is a view in perspective of the distributor of FIG. 1.
Figure 2B:
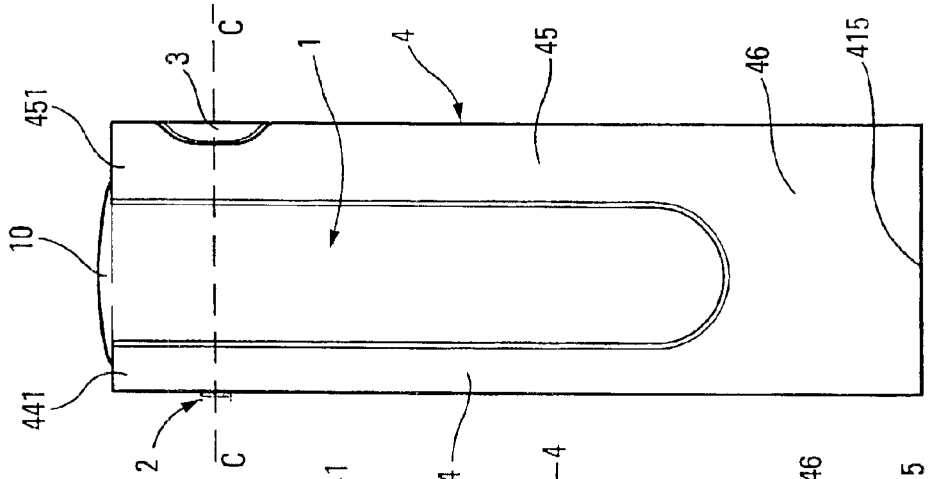
FIGS. 2*a* and 2*b* are lateral views of an embodiment variant of the distributor of FIG. 1.
Figure 2A:
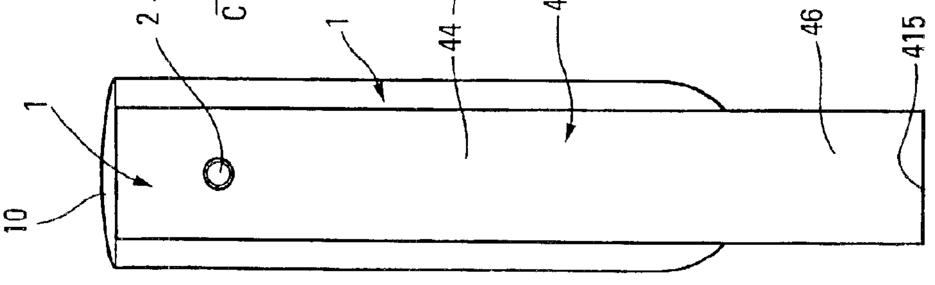

According to a characteristic common to the two embodiments of FIGS. 3 and 2*a*, 2*b*, the body forms a base 46 and two lateral uprights 44 and 45 which extend from the base 46 to be substantially parallel upwards. Advantageously, the base 46 forms a support surface 415 on which the distributor can be maintained upright in a stable way: this is precisely what gives the distributor this general form of a vertical column. The two uprights 44 and 45 are thus each linked by a lower extremity to the base 46 each with a free upper extremity 441, 451, seen on FIG. 2*b*. The uprights 44 and 45 extend on either side of the reservoir 1 substantially in the same direction. In fact, as can be seen in most of the figures, the reservoir 1 has a generally elongated shape with a bottom 10, lateral walls 11 and a neck 12 defining an opening. Advantageously the reservoir is placed inverted between the two uprights 44 and 45, that is to say with its neck 12 located at the very bottom, and set inside the base 46. The bottom 10 of the reservoir 1 can then advantageously be substantially aligned with the free extremities of the uprights 44 and 45 to form a sort of substantially plane upper wall.

Advantageously, the activating button 3 and the distribution outlet 2 are located near the free extremities 441, 451 of the uprights 44 and 45. This further raises the surprising visual effect of the distributor since the reservoir 1 clearly separates the activating button from the distribution outlet. In fact, the button and the outlet are then relatively far from the base 46 which forms the linkage element between the two uprights 44 and 45. It is also to be noted that it is advantageous to produce the base 46 with a minimum height to further augment the effect of practically complete separation of the two uprights 44 and 45. In this context, it is preferable that the base is no greater than half the total height of the distributor.

According to another interesting characteristic of the invention, the activating button and the distribution outlet are located substantially at the same height. More precisely, the activating button defines a push axis and the distribution outlet defines a distribution axis. It is then advantageous to merge these two axes so that the activating button 3 gives the impression of generating a distribution at the level of the outlet 2 passing directly through the reservoir 1, which is totally impossible.

In other terms, it can be said that the body 4 has a deep elongated channel defined laterally by the uprights 44 and 45 and below by the base 46. The reservoir 1 is housed in this deep channel without showing its opening 12. Consequently, it is impossible to know where the fluid product in the reservoir comes from. For the user, the reservoir is seen in the form of a recipient, advantageously transparent or translucent, without any opening. This increases even further the surprising visual effect linked to the positioning of the button and the outlet on either side of this reservoir.

Evidently, the positioning of the button 3 and the outlet 2 near the free extremities 441 and 451 must not be considered as limiting. On the contrary, the button 3 and the outlet 2 can be placed in any place or height whatsoever on the uprights 44 and 45 separated by the reservoir 1. The outlet can be placed near the extremity 441 while the button 3 can be placed near the base 46, or the inverse. The button 3 and the outlet 2 can also be placed close to the base 46.

In the embodiment of FIGS. 2*a*, 2*b* and 2*c*, it must be noted that the reservoir 1 has a circular transversal cross-section: this is more visible in FIG. 2*c*. As for the uprights 44 and 45, each has an internal wall curved in a manner corresponding to that of the reservoir such that the reservoir fits perfectly between the uprights. This also the case in the embodiment of FIG. 3 where the reservoir has a transversal cross-section substantially in an I shape.

In the two embodiments, the reservoir can be removable and replaceable; for this, the reservoir must be able to be inserted into the channel formed between the two uprights. The advantage of the shape of embodiment of FIG. 2*c* is that the reservoir can be fixed by screwing into the base. With the form of embodiment of FIG. 3, the reservoir has to be fixed by translational insertion. Furthermore, a reservoir circular in shape is easier to manufacture.

Figure 1:
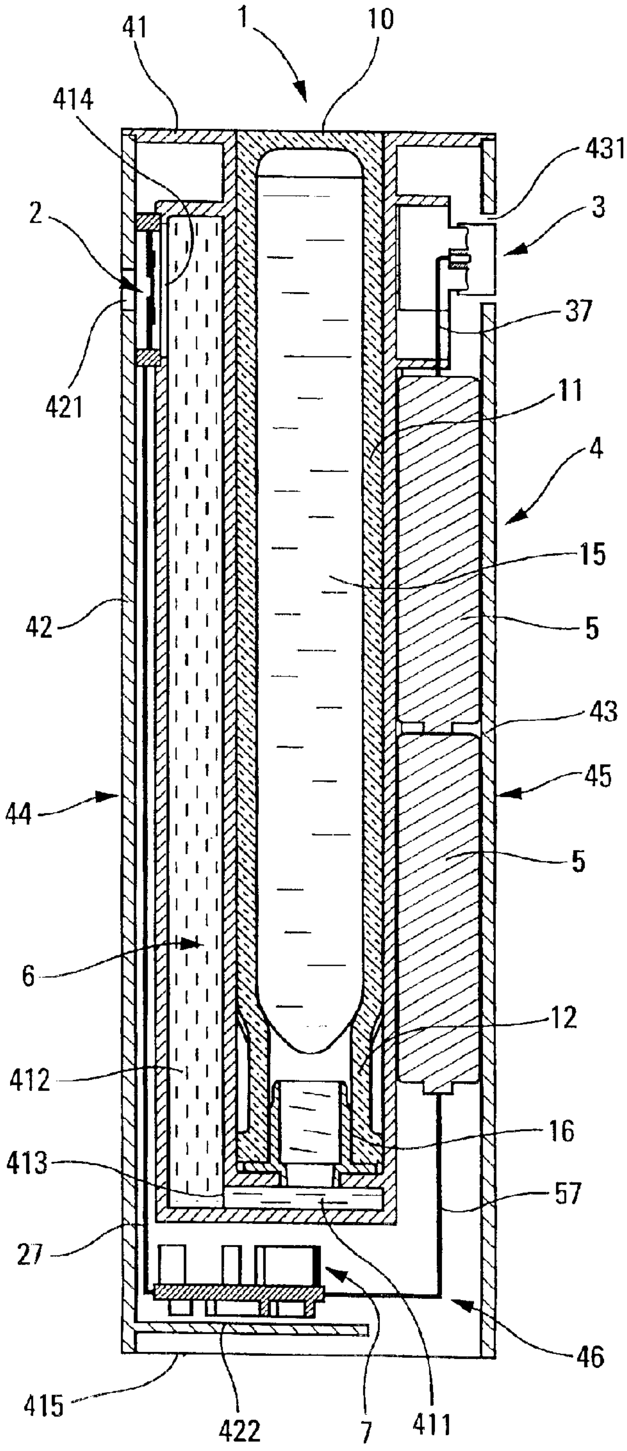
FIG. 1 is a vertical cross-section through a fluid product distributor according to the invention.
Figure 4:
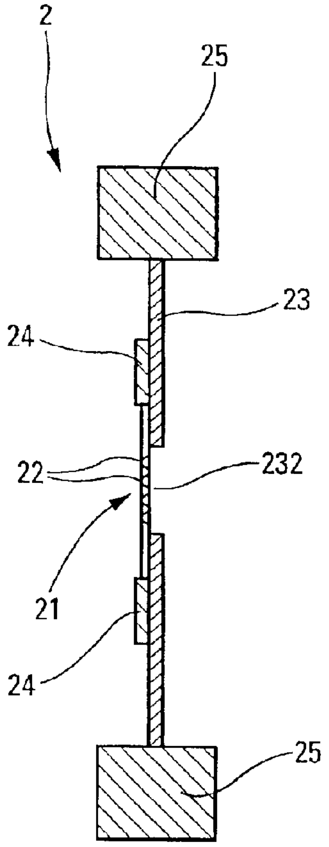
FIG. 4 is a greatly expanded view of the distribution means and the distribution outlet of the distributor of FIG. 1.

Above we have concentrated on a detailed description of the internal structure of a distributor of fluid product according to the invention. With reference to FIGS. 1 and 4, a special embodiment will now be described showing the internal structure of a fluid product distributor according to the invention. In this embodiment example, the uprights 44 and 45 together with the base 46 serve as a case intended to receive the different constitutive elements allowing the distribution of the fluid product initially stored in the reservoir 1 through the distribution outlet 2. The body 4, that is to say the two uprights 44, 45 and the base 46, can for example be made in three parts, that is a central part 41 to which two lateral walls 42 and 43 are added. These three elements can for example be made out of injected plastic material. The central part 41 defines the deep elongated channel inside which the reservoir 1 is fitted. The central part 41 forms a part of the uprights 44 and 45. The lateral walls 42 and 43 serve to complete the central part to thus form the two uprights 44 and 45 as well as the base 46. The lateral walls 42 and 43 can for example be fixed to the central part by a clipping system or by welding, gluing etc. The distributor shown in FIG. 1 corresponds to that of FIG. 3: one can thus see that the lateral walls 42 and 43 can be made in the form of plane plates which are then added onto the central part 41. The lateral wall 42 defines an opening 421 behind which the distribution outlet 2 is set. The detailed structure of the distribution outlet as well as the means of distribution will be given below with reference to FIG. 4. The lateral wall 42 also comprises a bottom 422 intended to support an electronic control circuit 7. As for the lateral wall 43, it is also formed with a bore 431 into which the activating button 3 is inserted. The activating button can be of the touch contact type. The lateral wall 43, with the central part 41, forms the lateral upright 45. This lateral upright 45 acts as a housing for the activating button and its associated mechanism as well as for the supply batteries 5. It is understood that one could imagine a single battery or any other means of electrical supply as for example accumulators associated with a solar panel or more simply a supply cable to be plugged into the electricity supply. In the lateral upright 44 formed by assembling the lateral wall 42 on the central part 41, the central part 41 forms a duct 412 which is open at the level of its lower extremity 413 and at the level of its upper extremity 414. This duct 412 is intended to contain a capillary wick 6. At its lower extremity, the duct 412 communicates with a chamber 411, which itself communicates with the opening 12 of the reservoir 1. Advantageously, a controlled sealing system can be set at the level of the opening 12, for example inside a sleeve 16 inserted into the opening 12. Thus, the fluid product 15 stored in the reservoir 1 can only run selectively under gravity into the chamber 411. Advantageously, the chamber 411 can contain a foam material allowing a certain quantity of fluid product to be retained by impregnation. Consequently, when the fluid product in the reservoir 1 reaches the chamber 413, it soaks the capillary wick 6 with the result that the fluid product rises inside the capillary wick 6 as far as its upper extremity 414. As described above, the duct 412 is open near its upper extremity 414 in such a way as to communicate directly with the distribution means 2 which are more visible in FIG. 4.

In this particular embodiment, the distribution means can be similar or identical to those described in document EP-0 615 470. In this case, the distribution means used in the distributor of the present invention comprise a plate or a membrane 21 perforated by several distribution holes 22 which together constitute the distribution outlet. This membrane 21 is associated with vibration means which are shown here in the form of a substrate 23 on which a vibrator element 24 is applied, such as a piezoelectric element. More precisely, the substrate 23 comes in the form of a disc or a washer defining a central circular opening 232. The vibrator element 24 can also be in the form of a washer fixed on the annular substrate 23. As for the perforated membrane 21, it covers the central opening 232 of the substrate 23. By applying a voltage to the vibrator element 24, the membrane 21 begins to vibrate, which allows the expulsion of the fluid product located just behind it, in the form of fine droplets. All this distribution technique is clearly defined in the prior art document mentioned above.

According to the invention, the substrate 23 is mounted in a support element 25 of annular shape, or generally of the same shape as the substrate 23. In fact, substrate 23 can be square or rectangular in shape. The support element 25 is made out of a material being both leak-proof for the liquid as well as damping down the vibrations generated by the vibrator element 24. In this particular form of distribution means, the distribution outlet is an integral part of the distribution means. The support element 25 with its substrate, its vibrator element and its perforated membrane is set in the upright 44 at the level of the upper opening of the duct 412 in such a way that the distribution holes 22 of the perforated membrane 21 are facing the opening 421 formed in the lateral wall 42 added onto the central element 41. The support element 25 makes the outlet opening 414 of the duct 412 leak-proof, given that the fluid product is present and in contact with the substrate 23 and the perforated membrane 21, brought to this position by the capillary wick 6. The capillary wick 6 can come directly from the perforated membrane 21 or, as a variant, a foam material can be interposed between the vibrating membrane 21 and the capillary wick 6. The support element 25 is mounted in the upright 44 by being caught between the opening 414 of the duct 412 and the internal surface of the lateral wall 42 around the opening 421. The element 25 is then fixed in position in the distributor, and prevents vibrations generated by the vibrator element 24 from propagating throughout the whole of the distributor. Thus the fluid product stored in the reservoir 1 can be transported to the internal wall of the vibrating membrane 21 through the chamber 413, through the capillary wick 6 without risk of leakage. Downstream, the sleeve 16 inserted in the neck 12 of the reservoir makes the central part 21 leak-proof at the level of the bottom of the channel, and upstream, the support element 25 makes the level of the outlet leak-proof.

The vibrator element 24 needs a voltage supply, which is why it is linked electrically to an electronic control circuit 7 by supply wires 27. In a corresponding way, the contact mechanism of the activating button 3 as well as the dry cells or batteries 5 are connected to the electronic control circuit 7 by supply cables 47 and 57.

Thanks to the capillary wick system 6, the fluid is fed to the perforated membrane 21 which can be made to vibrate by applying a voltage to the vibrator element 24. This supply voltage is delivered when one presses on the activating button 3 which then closes the circuit which passes through the electronic control system 7. Thus, fluid product is distributed in a continuous manner in the form of fine pulverised droplets at the level of the distribution outlet by the network of 22 holes made in the perforated vibrating membrane 21. The user simply presses on the activating button 3, and as a result, a jet of pulverised product is created at the outlet 2. The user simply and immediately notes the surprising effect linked to the interposition of the reservoir 1 which is preferably transparent.

What is claimed is:

1. Fluid product distributor comprising:

a reservoir of fluid product, a distribution outlet, distribution means for distributing fluid product through the distribution outlet, and an activating button to activate the means of distribution, characterised in that the reservoir is visible and the distribution outlet and the activating button are located on either side of the reservoir, such that the reservoir visibly extends between the distribution outlet and the activating button; and wherein the fluid product distributor further comprises two uprights extends on either side of the reservoir, one upright receiving the distribution outlet and the other upright receiving the activating button.

2. Distributor according to claim 1, in which the reservoir is made out of a transparent or translucent material.

3. Distributor according to claim 1, in which the uprights are connected together at the level of a base.

4. Distributor according to claim 3, in which the uprights and the base are produced in the form of a body.

5. Distributor according to claim 3, in which the uprights form therebetween a deep elongated channel limited laterally by the uprights and below by the base, the reservoir being housed in this channel.

6. Distributor according to claim 3, in which the base forms a support surface on which the distributor stands straight in a stable manner with the uprights oriented substantially vertical.

7. Distributor according to claim 3, in which the uprights each comprise an extremity linked to the base and a free extremity.

8. Distributor according to claim 7, in which the reservoir comprises an opening set in the base and a bottom located substantially at the level of the free extremities of the uprights.

9. A fluid product distributor comprising:

a reservoir of fluid product, a distribution outlet, distribution means for distributing fluid product through the distribution outlet, and an activating button to activate the means of distribution; and wherein the reservoir is visible and the distribution outlet and the activating button are located on either side of the reservoir, such that the reservoir visibly extends between the distribution outlet and the activating button; and in which the distribution outlet defines a distribution axis and the activating button defines a push axis, the distribution axis and the push axis being parallel and advantageously aligned.

10. Distributor according to claim 7, in which the distribution outlet and the activating button are located near the free extremities of the uprights.

11. Distributor according to claim 1, in which the distribution outlet comprises a vibrating plate perforated by several outlet holes.

12. Distributor according to claim 11, in which the distribution means comprise drive means to make the perforated plate vibrate.

13. Distributor according to claim 11, comprising a capillary supply system of fluid product to bring fluid product from the reservoir to the perforated plate.

14. Distributor according to claim 13, in which the upright receiving the distribution outlet contains a capillary wick linking the reservoir to the perforated plate.

15. Distributor according to claim 1, in which the reservoir is removable.

16. Distributor according to claim 1, in which the reservoir has a circular transversal cross-section.

17. The distributor according to claim 9, comprising two lateral uprights that extend on either side of the reservoir, one upright receiving the distribution outlet and the other upright receiving the activating button.

18. The distributor according to claim 9, in which the distribution outlet comprises a vibrating plate perforated by several outlet holes.

19. The distributor according to claim 18, comprising a capillary supply system of fluid product to bring fluid product from the reservoir to the perforated plate.

20. The distributor according to claim 9, in which the reservoir is removable.

21. The distributor according to claim 9, in which the reservoir has a circular transversal cross-section.

22. A fluid product distributor comprising:

a reservoir of fluid product, a distribution outlet, an activating button; and a coupling between the distribution outlet and the activating button;

wherein activation of the activating button distributes fluid product through the distribution outlet;

wherein the reservoir is visible and the distribution outlet and the activating button are located on either side of the reservoir, such that the reservoir visibly extends between the distribution outlet and the activating button; and wherein the fluid product distributor further comprises two lateral uprights that extend on either side of the reservoir, one upright receiving the distribution outlet and the other upright receiving the activating button.

* * * * *